(12) United States Patent
Hetzer et al.

(10) Patent No.: US 9,789,270 B2
(45) Date of Patent: Oct. 17, 2017

(54) INHALATION THERAPY DEVICE COMPRISING AN AMPOULE FOR STORING A MEDICAMENT TO BE NEBULIZED

(75) Inventors: Uwe Hetzer, Munich (DE); Thomas Gallem, Munich (DE)

(73) Assignee: PARI Pharma GmbH, Starnberg (DE)

( * ) Notice: Subject to any disclaimer, the term of this patent is extended or adjusted under 35 U.S.C. 154(b) by 1536 days.

(21) Appl. No.: 11/990,474

(22) PCT Filed: Aug. 16, 2006

(86) PCT No.: PCT/EP2006/008086
§ 371 (c)(1),
(2), (4) Date: Jul. 13, 2009

(87) PCT Pub. No.: WO2007/020073
PCT Pub. Date: Feb. 22, 2007

(65) Prior Publication Data
US 2009/0293868 A1   Dec. 3, 2009

(30) Foreign Application Priority Data
Aug. 16, 2005   (DE) .................... 10 2005 038 619

(51) Int. Cl.
*A61M 15/00*   (2006.01)

(52) U.S. Cl.
CPC .... *A61M 15/0085* (2013.01); *A61M 15/0036* (2014.02); *A61M 15/0086* (2013.01); *A61M 2206/14* (2013.01)

(58) Field of Classification Search
CPC .......... A61M 15/0085; A61M 15/0036; A61M 2206/14; A61M 15/0086; A61M 11/005;
(Continued)

(56) References Cited

U.S. PATENT DOCUMENTS

| 3,171,412 A | 3/1965 | Braun |
|---|---|---|
| 3,919,374 A | 11/1975 | Komendowski |

(Continued)

FOREIGN PATENT DOCUMENTS

| AU | WO 2005028006 A1 * | 3/2005 | ............ A61M 15/00 |
|---|---|---|---|
| CA | 2 619 605 A1 | 2/2007 | |

(Continued)

OTHER PUBLICATIONS

International Preliminary Report on Patentability mailed Feb. 28, 2008 from International Application No. PCT/EP2006/008086.
(Continued)

*Primary Examiner* — Kathryn E Ditmer
(74) *Attorney, Agent, or Firm* — Wolf, Greenfield & Sacks, P.C.

(57) ABSTRACT

An inhalation therapy device includes an atomizer for atomizing a drug which is advantageously present in the form of a fluid into an atomization chamber so that an aerosol or mist is provided in the atomization chamber. The patient or user can inhale the aerosol produced by the atomizer from the atomization chamber via a mouthpiece. The ampoule is inserted into an ampoule holder holding the fluid-containing ampoule. The inhalation therapy device also includes an opening unit for opening the fluid-containing ampoule. The ampoule holder advantageously includes a first part, disposed displaceably in relation to the opening unit, thereby allowing an ampoule present in the ampoule holder to be displaced in the direction of the opening unit.

17 Claims, 9 Drawing Sheets

Figure 4A:
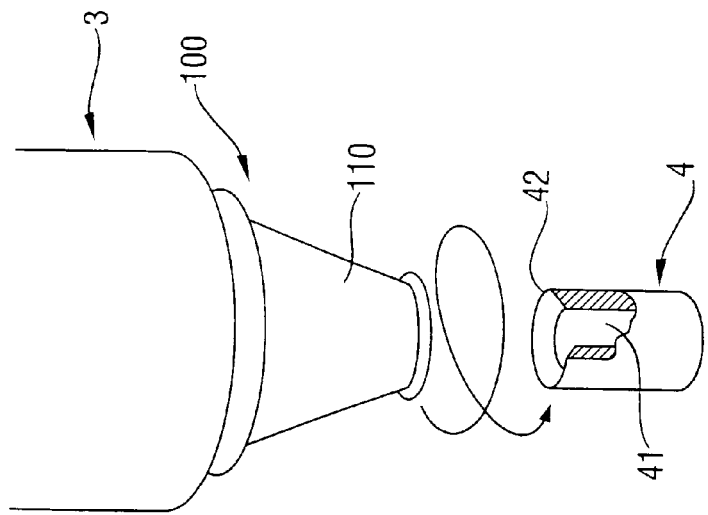

(58) Field of Classification Search
CPC .............. A61M 11/006; A61M 11/008; A61M 15/0028; A61M 15/003; A61M 15/0033; A61M 15/0035; A61M 15/0038; A61M 15/004; A61M 15/0041; A61M 16/10; A61M 16/104; A61M 16/108; A61M 16/1085; A61M 16/14; A61M 16/16; A61M 16/18; B05B 7/00; B05B 7/04; B05B 7/0416; B05B 17/00; B05B 17/06; B05B 17/0607; B05B 17/0638; B05B 17/0646
USPC .............. 128/200.14, 207.27, 207.2, 207.19, 128/207.12; 206/528, 532, 828
See application file for complete search history.

(56) References Cited

U.S. PATENT DOCUMENTS

| | | | |
|---|---|---|---|
| 4,133,312 A | 1/1979 | Burd | |
| 4,671,763 A | 6/1987 | Weiler | |
| 4,995,511 A | 2/1991 | Evans | |
| 5,009,309 A | 4/1991 | Hansen | |
| 5,048,514 A | 9/1991 | Ramella | |
| 5,152,284 A | 10/1992 | Valentini et al. | |
| 5,337,740 A | 8/1994 | Armstrong et al. | |
| 5,379,898 A | 1/1995 | Joulia | |
| 5,435,282 A * | 7/1995 | Haber | A61M 15/0065 128/200.14 |
| 5,515,842 A | 5/1996 | Ramseyer et al. | |
| 5,529,059 A | 6/1996 | Armstrong et al. | |
| 5,619,985 A | 4/1997 | Ohki et al. | |
| 5,647,349 A | 7/1997 | Ohki et al. | |
| 5,715,810 A | 2/1998 | Armstrong et al. | |
| 5,921,236 A | 7/1999 | Ohki et al. | |
| 5,950,619 A | 9/1999 | van der Linden et al. | |
| 5,970,974 A | 10/1999 | Van Der Linden et al. | |
| 6,059,749 A | 5/2000 | Marx | |
| 6,145,703 A * | 11/2000 | Opperman | A61M 15/0065 222/153.13 |
| 6,197,260 B1 | 3/2001 | Bradshaw et al. | |
| 6,367,473 B1 | 4/2002 | Käfer | |
| 6,443,152 B1 | 9/2002 | Lockhart et al. | |
| 6,481,435 B2 | 11/2002 | Hochrainer et al. | |
| 6,668,827 B2 | 12/2003 | Schuler et al. | |
| 6,708,846 B1 | 3/2004 | Fuchs et al. | |
| 6,832,703 B1 | 12/2004 | Scott et al. | |
| 6,851,626 B2 | 2/2005 | Patel et al. | |
| 6,877,672 B2 | 4/2005 | Stihl | |
| 6,948,491 B2 | 9/2005 | Loeffler et al. | |
| 6,948,494 B1 | 9/2005 | Snow | |
| 6,971,385 B1 | 12/2005 | Flora | |
| 7,032,590 B2 | 4/2006 | Loeffler et al. | |
| 7,040,316 B2 | 5/2006 | Connelly et al. | |
| 7,100,600 B2 | 9/2006 | Loeffler et al. | |
| 7,185,790 B2 | 3/2007 | Weiler | |
| 7,261,102 B2 | 8/2007 | Barney et al. | |
| 7,270,127 B2 | 9/2007 | Lockhart et al. | |
| 7,360,536 B2 | 4/2008 | Patel et al. | |
| 7,681,571 B2 * | 3/2010 | Makinson | A61M 16/10 128/200.24 |
| 8,047,394 B2 * | 11/2011 | Hansen | 220/284 |
| 8,074,642 B2 | 12/2011 | Bruce | |
| 2002/0129812 A1 * | 9/2002 | Litherland | A61M 11/005 128/200.14 |
| 2002/0134372 A1 * | 9/2002 | Loeffler et al. | 128/200.14 |
| 2003/0140921 A1 | 7/2003 | Smith et al. | |
| 2004/0126325 A1 | 7/2004 | Lewis et al. | |
| 2005/0051166 A1 | 3/2005 | Glusker et al. | |
| 2005/0056281 A1 | 3/2005 | Snow | |
| 2005/0150492 A1 * | 7/2005 | Dunkley et al. | 128/203.21 |
| 2005/0161041 A1 | 7/2005 | Schuler et al. | |
| 2005/0263618 A1 * | 12/2005 | Spallek | A61M 15/0065 239/433 |
| 2006/0054165 A1 * | 3/2006 | Hughes | A61M 15/009 128/200.14 |
| 2006/0057257 A1 | 3/2006 | Ma | |
| 2006/0150969 A1 | 7/2006 | Connelly et al. | |
| 2007/0107720 A1 | 5/2007 | Boeck et al. | |
| 2009/0137950 A1 | 5/2009 | Loenner et al. | |

FOREIGN PATENT DOCUMENTS

| | | | |
|---|---|---|---|
| DE | 38 23 428 A1 | 1/1990 | |
| DE | 38 33 036 A1 | 4/1990 | |
| DE | 43 06 458 A1 | 9/1994 | |
| DE | 102 53 237 A1 | 5/2004 | |
| EP | 0 326 391 A2 | 8/1989 | |
| EP | 1 186 530 A1 | 3/2002 | |
| EP | 1186350 A1 * | 3/2002 | B05B 17/00 |
| JP | 50-64490 U | 10/1973 | |
| JP | 3094233 U | 9/1991 | |
| JP | 10-151199 | 6/1998 | |
| JP | 10-179739 | 7/1998 | |
| JP | 2003-521977 A | 7/2003 | |
| WO | WO 00/66277 A1 | 11/2000 | |
| WO | WO 01/58236 A2 | 8/2001 | |
| WO | WO 02/074373 A1 | 9/2002 | |
| WO | WO 02/074374 A1 | 9/2002 | |
| WO | WO 02074372 A2 * | 9/2002 | A61M 11/005 |
| WO | WO 2006006963 A2 * | 1/2006 | A61M 15/0065 |
| WO | WO 2006/032320 A1 | 3/2006 | |
| WO | WO 2007/020073 A1 | 2/2007 | |

OTHER PUBLICATIONS

Search Report mailed May 7, 2009 from European Application No. 08169011.

English Translation of Examination Report dated Mar. 19, 2013 from Japanese Application No. 2010-286147.

* cited by examiner

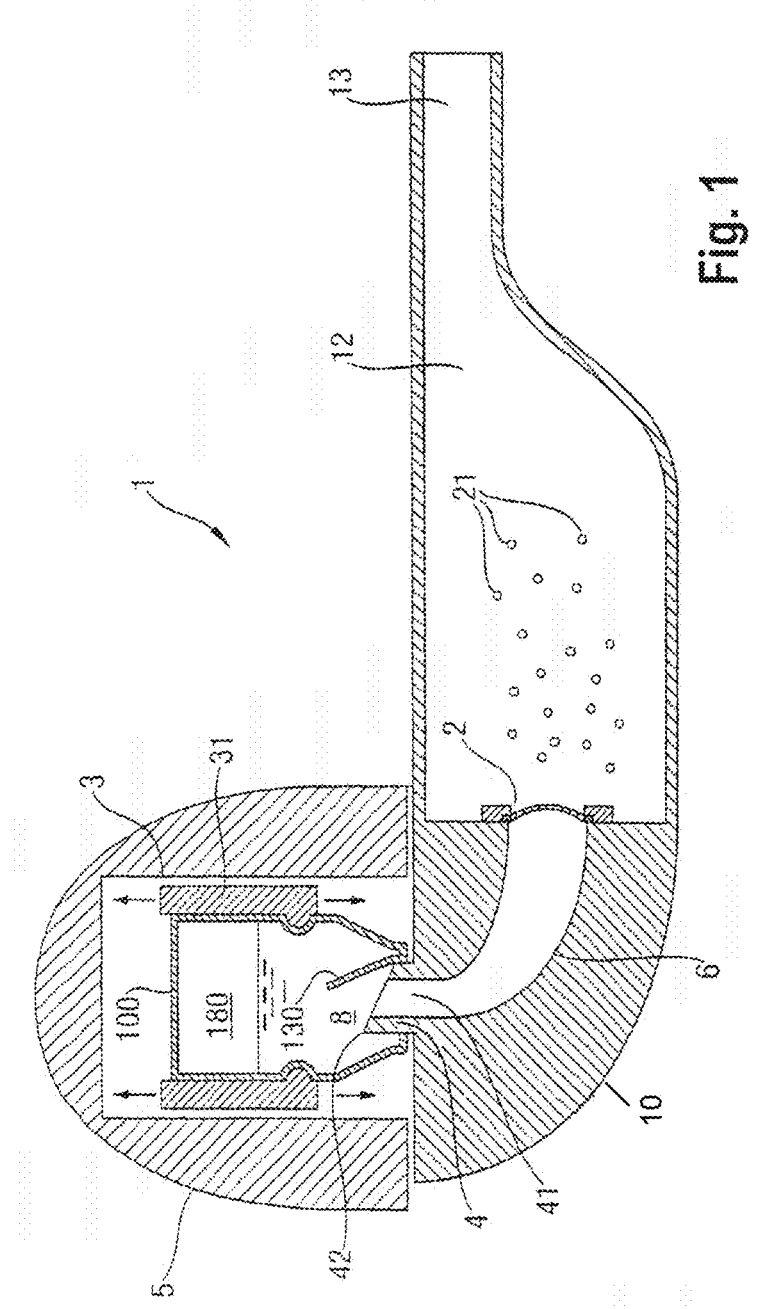

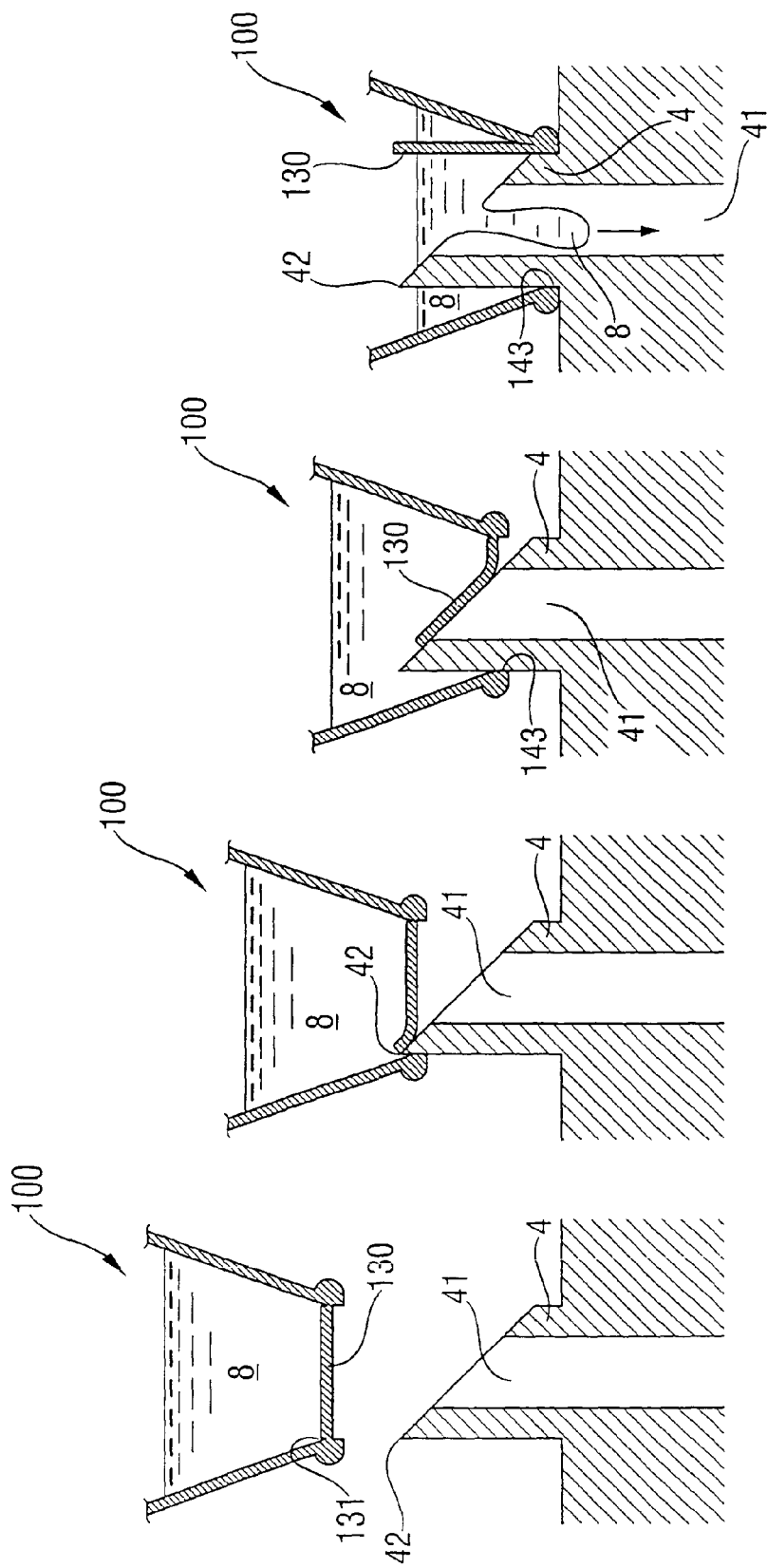

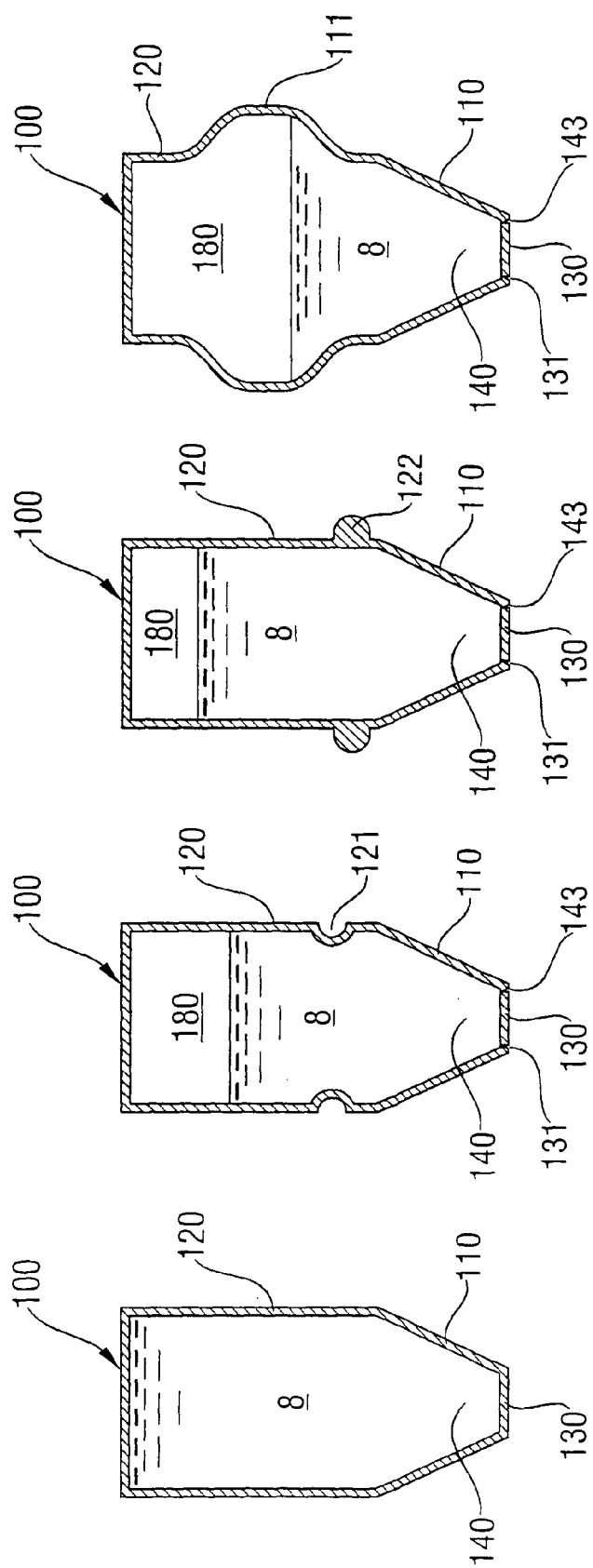

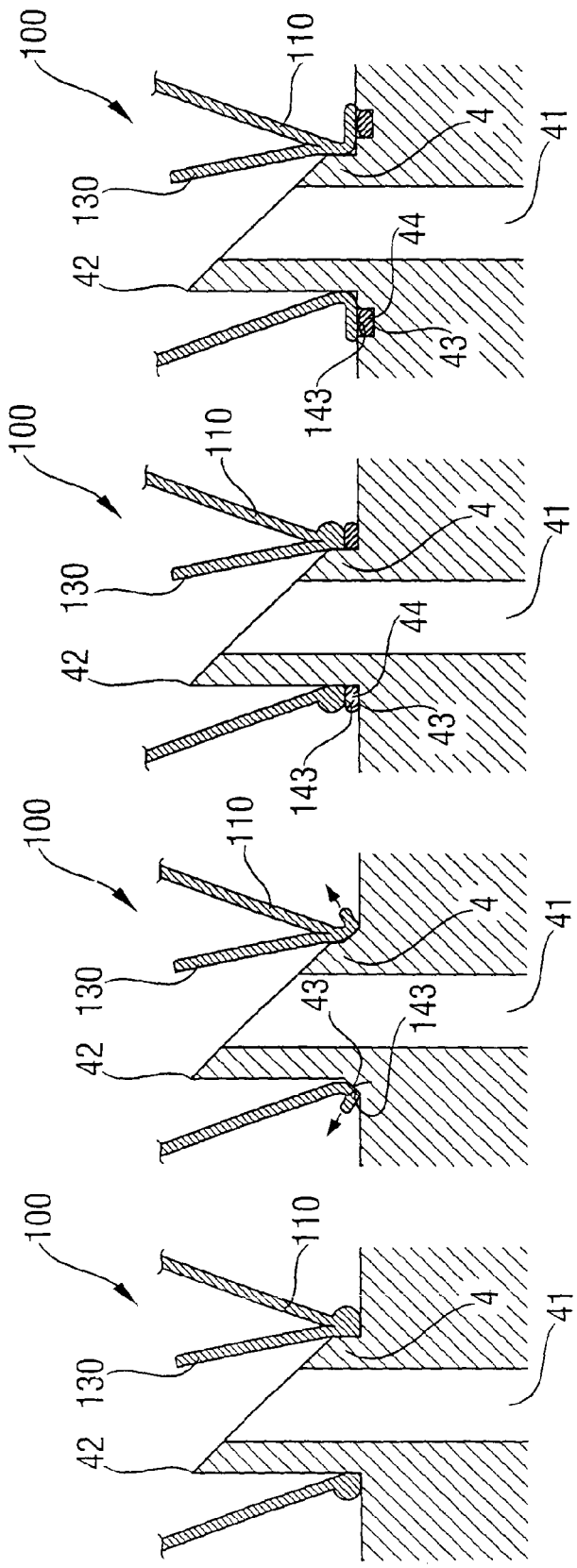

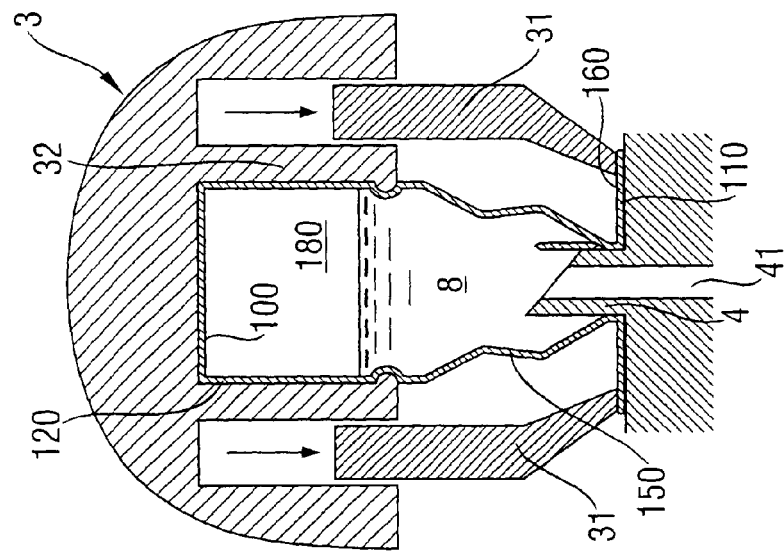
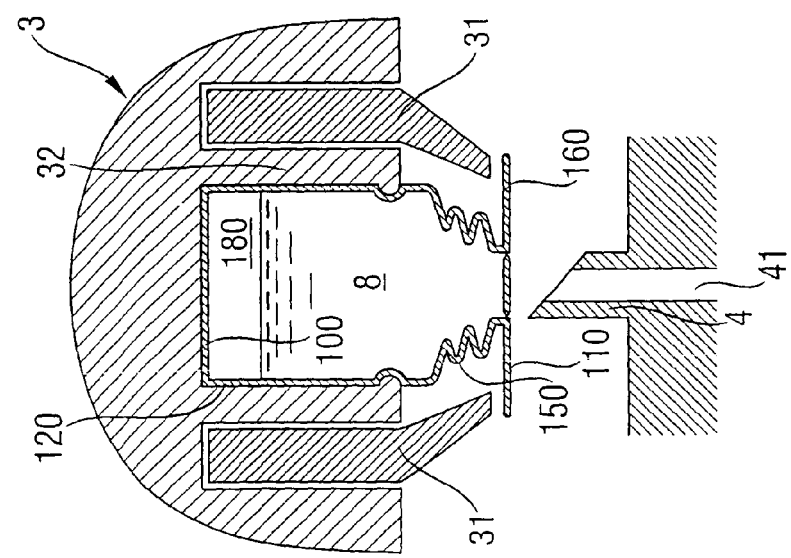

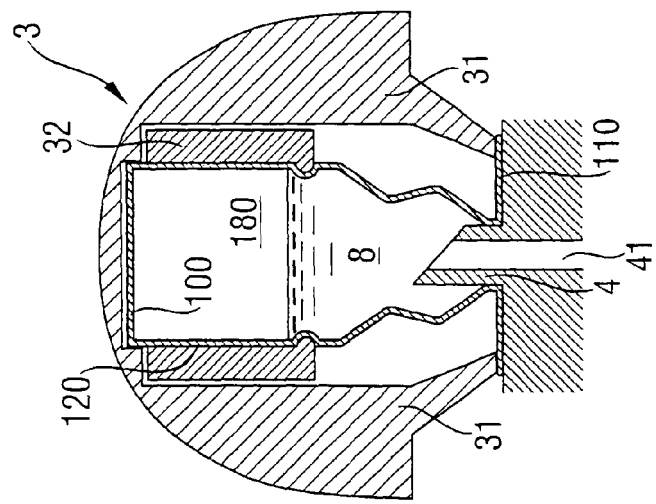
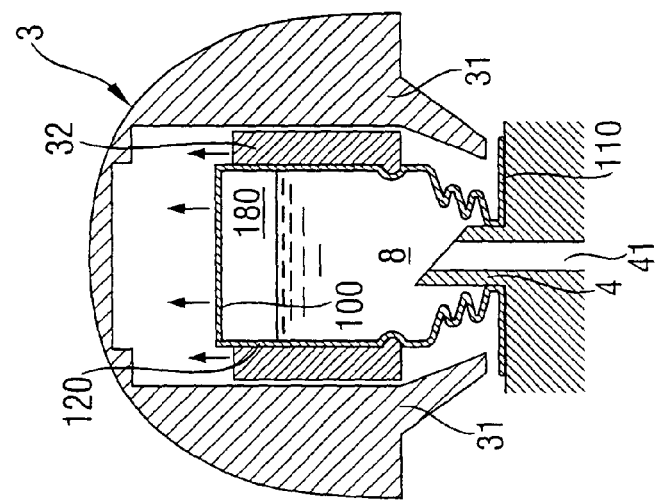
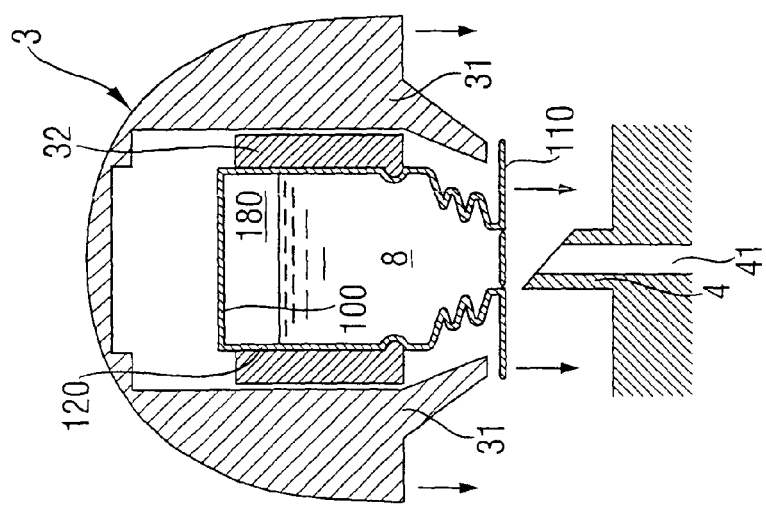
Fig. 8c
Fig. 8b
Fig. 8a

INHALATION THERAPY DEVICE COMPRISING AN AMPOULE FOR STORING A MEDICAMENT TO BE NEBULIZED

The present invention relates to inhalation therapy devices in which a medicament to be nebulised is stored in an ampoule that can be inserted in the inhalation therapy device.

Aerosols for therapeutic purposes, some of which have to meet very high requirements, are generated with inhalation therapy devices. The requirements arise from the treatment to be performed with the inhalation therapy device. One of the requirements concerns dosing precision, i.e. the precision of the administered quantity of the medicament provided as an aerosol. Only if the dose of a medicament administered to the patient is precisely established can effective treatment with highly effective medicaments be carried out. One of the basic conditions influencing dosage precision is the quantity of fluid to be nebulised that is placed in the inhalation therapy device.

One approach for ensuring a predetermined fill quantity is to give the user of the inhalation therapy device an ampoule which contains a quantity of fluid precisely determined in production of the ampoule and which the user places in the device in preparation for the inhalation therapy session.

An inhalation therapy device with such an ampoule is described in WO 02/074374 A and in US 2003/0140921 A. After the ampoule has been opened by the user, it is inserted from above into an ampoule holder that is provided in the nebuliser device. After insertion of the ampoule, the fluid stored in the ampoule is supplied to the aerosol generator of the nebuliser.

The design of known ampoules is disadvantageous in various respects. Firstly, when the user opens the ampoule, the content of the ampoule can be contaminated. Secondly, fluid can be lost when the ampoule is inserted in the therapy device. Finally, it cannot be ensured with the certainty necessary for high dosage precision that all of the fluid filled in the ampoule will pass from the ampoule to the aerosol generator of the therapy device for nebulisation.

Against this background, the object to be solved by the invention is to provide an inhalation therapy device comprising an ampoule for storing a medicament to be nebulised, which does not have the described disadvantages and with which a higher dosage precision is achieved.

The object of the present invention is solved by an inhalation therapy device having the features of claim 1 and/or an ampoule having the features of claim 16. Advantageous embodiments arise from the sub-claims.

An inhalation therapy device according to the invention comprises a nebuliser device for nebulising a fluid supplied thereto and for generating an aerosol, an ampoule holder for retaining a fluid-containing ampoule and an opening means for opening said fluid-containing ampoule. According to the invention, the opening means and a first part of the ampoule holder are arranged so as to be displaceable in relation to one another such that upon displacement, the opening means opens an ampoule disposed in the ampoule holder and thus a fluid contained in said ampoule reaches the nebuliser device. It is thereby achieved that opening of the ampoule no longer has to be carried out by the user before inserting the ampoule in the inhalation therapy device. The user can rather insert the ampoule in the ampoule holder and open said ampoule using the opening means, which is part of the inhalation therapy device, by displacing the opening means in relation to the ampoule holder. Displacement can be achieved in various ways, however according to the invention, it usually take place only after insertion of the ampoule into the inhalation therapy device, more precisely into the ampoule holder of the inhalation therapy device.

At this point it should be stated that the term ampoule is to be understood as any type of container or reservoir in which a medicament can be stored. An ampoule can consist in particular of various materials, for example plastic, glass, metal or other suitable materials. In particular, an ampoule can also consist of different materials in sections. For example, a glass ampoule can be sealed with a plastic seal or different areas of the ampoule can be made of different plastics which are accordingly selected depending on their use at the corresponding ampoule areas.

According to an advantageous embodiment, the ampoule holder is disposed in a lid of the inhalation therapy device. This ensures that the user, on closing the inhalation therapy device, correctly places the ampoule, which is in the ampoule holder in the lid, in the inhalation therapy device and that the user also need only handle a minimum number of components, for example the inhalation therapy device with its lid.

According to a further advantageous embodiment, the opening means for opening the fluid-containing ampoule is formed as a needle. The ampoule, if appropriately formed, can be opened relatively easily in this manner without needing to provide complex mechanics. The ampoule can be punctured by the needle in an appropriately formed area and hence opened, for example in a thin-walled sealing area made of plastic.

According to a further advantageous embodiment, the inhalation therapy device is furthermore provided with a supply means for supplying a fluid to be nebulised to the nebuliser device, with the fluid reaching the nebuliser device through the supply means. In this way, the nebuliser device does not necessarily need to be provided immediately next to the opening means but can also be provided remote from the opening means, in particular if the alignment of the opening means and the alignment of the nebuliser device differ. The supply means then not only acts as a conduit but also allows the alignment of the opening means and that of the nebuliser device to be arbitrarily selected in order to adapt it to local conditions.

According to a further advantageous embodiment, the opening means comprises a conduit that extends at least partly in the longitudinal direction of the opening means, through which conduit the fluid passes from the ampoule to the nebuliser device or supply means. In particular if the opening means is formed as a needle, the fluid can, if an appropriately designed ampoule is punctured, pass, after puncturing, through the conduit formed as a channel inside the needle to the nebuliser device or supply means. The problem of sealing when opening the ampoule can be easily solved in this manner.

According to a further advantageous embodiment, the opening means and the first part of the ampoule holder are displaceable along a substantially straight, circular or helical path. By way of linear displacement, the seal between the ampoule and the opening means can be maintained throughout the opening process, if the ampoule is appropriately designed, so that none of the medicament in the ampoule can be lost. A substantially circular displacement is particularly advantageous in the case of an opening movement in the tangential direction or if part of a correspondingly designed ampoule is sheared off for opening. In the case of a substantially helical opening displacement, the substantially linear and substantially circular opening movements can be combined, which is particularly advantageous when closing the lid of the inhalation therapy device by means of a screw thread. In the case of a substantially straight displacement, the axial movement can be used for a bayonet closure, while in the case of a substantially circular movement the rotation movement following the axial movement can be used for a bayonet closure.

According to a further advantageous embodiment, the opening means has a cutter which is designed to cut, when displacement occurs, into a wall area of the ampoule intended for opening. A cutter allows a substantially predictable opening which can be produced in an accordingly precise manner so that a reliable seal can be achieved during the opening movement in this case as well. Furthermore, the opening movement can be carried out in a controlled manner such that given an appropriate design of the cutter and the ampoule, it can be prevented that parts of the ampoule become detached or chip off and accidentally reach the nebuliser device, or in the worst case the respiratory tract of the patient. The cutter can be provided substantially in the axial direction, perpendicular to the axial direction or at an angle to the axial direction, depending on what is necessary to open a correspondingly designed ampoule.

According to a further advantageous embodiment, the opening means is integrally connected with the supply means. An opening means that is integral or connected in one piece with the supply means allows technically simple production of the inhalation therapy device with few components and without joints that are susceptible to contamination.

According to a further advantageous embodiment, the inhalation therapy device comprises a sealing device for sealing the ampoule against the opening means. Such a seal of the ampoule against the inhalation therapy device can prevent a fluid or medicament present in the ampoule from being lost, which would inevitably lead to poorer dosage accuracy, and as a result of the fluid or medicament could uncontrollably reach the exterior.

According to a further advantageous embodiment, the opening means is formed to seal the opening of the ampoule against the opening means. In this way, the seal can be provided as closely as possible to the opening means. As few surfaces and areas of the inhalation therapy device as possible come into contact with the fluid in the ampoule so that only small quantities of the fluid are lost for treatment owing to adhesion to external surfaces. The sealing means can be realised by explicit sealing elements such as O-rings, sealing lips or the like, or also by a precise fit between the ampoule and opening means.

According to a further advantageous embodiment, the inhalation therapy device comprises a squeezing means which is designed to create a positive pressure in the ampoule to squeezedly hold the ampoule in a displaced position. It can be achieved in this manner that on opening the ampoule, a gas or air that is contained in the ampoule alongside the fluid can escape. If the ampoule is sealed against the inhalation therapy device in the squeezed state after the escape of air or gas, and if squeezing is then stopped, a negative pressure prevails in the ampoule, which acts on the fluid in the ampoule even if it has already reached the nebuliser device. Such a negative pressure in the fluid reservoir has a particularly beneficial effect on the nebulisation results since, as can be proven, droplet formation on the side of the membrane of a membrane nebuliser that faces away from the supply means can be reduced.

According to a further advantageous embodiment, the ampoule holder constitutes the squeezing means and the squeezing means is formed such that it squeezes the ampoule during opening. In this way, the positive pressure generated in the ampoule can escape on opening, which is particularly advantageous if the ampoule orifice is held in a upwards-pointing position during this procedure, so that on opening, no fluid but only the gas in the ampoule can escape. On later sealing and subsequent release of the ampoule from the squeezing means, a negative pressure can be generated in the ampoule, which has proved particularly advantageous for nebulisation in the past since particularly good nebulisation results were achieved when the fluid was under negative pressure. Alternatively, the squeezing means can also be provided on the opening means so that the squeezing means is not fixed in relation to the displaceable part of the ampoule holder but in relation to the opening means. Thus, squeezing and subsequent release from squeezing can be achieved when the ampoule is pushed into the squeezing means.

According to a further advantageous embodiment, the first part of the ampoule holder is designed so that it only engages with the ampoule upon displacement.

According to a further advantageous embodiment, the ampoule holder comprises a second part which is designed to hold the ampoule. In this way, the ampoule can be introduced into another part of the ampoule holder which, for example, is not displaceable, so that the user can handle the ampoule in respect of a second stationary part of the ampoule holder and this part of the holder cannot move when positioning the ampoule. In this way, inter alia irritation for the user can be avoided if, for example, a moveable part in the lid of the inhalation therapy device moves back on insertion of the ampoule. Furthermore, the user is thereby given perceptible feedback with regard to complete opening and readiness of the device for use.

According to a further advantageous embodiment, the first part of the ampoule holder and the second part of the ampoule holder are formed so as to be displaceable in relation to each other so that the first part of the ampoule holder acting on a first area of the ampoule and the second part of the ampoule holder acting on a second area of the ampoule are moved in relation to one another when the first area and second area of the ampoule are displaced such that a negative pressure or positive pressure develops in the ampoule. This can achieve that, after insertion in the ampoule holder, an ampoule can be moved such that a negative pressure or positive pressure develops in the ampoule without the ampoule having to be opened beforehand. Such a design of ampoule holder allows, for example, a negative pressure to be generated in the ampoule even in the overhead position, and the ampoule to be reliably opened and sealed such that no fluid or medicament can be lost.

An ampoule according to the invention is designed for use in an inhalation therapy device as described above, wherein the ampoule comprises a first area designed for opening by the opening means and a second area designed for holding by the ampoule holder. In this way, an ampoule is provided which can be used in the inhalation therapy device described above and which, because of its design, advantageously does not need to be opened directly by the user himself but can rather be opened by an opening means of the inhalation therapy device. This avoids the user having to handle the opening of the ampoule himself directly. This allows improved dosage precision and handling safety when using the ampoule in the inhalation therapy device.

According to an advantageous embodiment, the ampoule has a sealing surface which is formed to seal the ampoule against the opening means or supply means. This can avoid a fluid or medicament disposed in the ampoule accidentally escaping from the ampoule and no longer being available for inhalation therapy. The sealing surface can be realised by an explicit sealing element such as an O-ring or sealing lip or the like. These sealing elements can also be formed directly on the ampoule. Alternatively, a correspondingly designed wall area of the ampoule can serve as the sealing element due to its elasticity when, for example, punctured by a needle.

According to a further advantageous embodiment, the first area of the ampoule is arranged so as to be displaceable in relation to the second area of the ampoule. This allows the volume of the ampoule to be enlarged or reduced in order to generate a positive or negative pressure in the ampoule, which, for example, has a positive effect for further nebulisation on the nebulisation result.

According to a further advantageous embodiment, the first area of the ampoule and the second area of the ampoule are joined together by a resilient element or bellows. In this way, the first area of the ampoule and the second area of the ampoule are moveable in relation to one another without the ampoule having to be opened and a fluid or medicament being lost. Thus, the volume of the ampoule can be enlarged or reduced without having to open the sealed ampoule.

According to a further advantageous embodiment, the ampoule is designed such that the second part of the ampoule absorbs tensile forces upon engagement of the ampoule holder. In this way, it is possible to hold the first area of the ampoule in its position in relation to the second area of the ampoule after displacement with respect to one another in order to maintain a positive or negative pressure which was generated in the ampoule by the displacement. Furthermore, with an ampoule in which a negative pressure was generated, it is possible, given an appropriate design of the ampoule and the opening means, to maintain the negative pressure state even when the ampoule is in the opened state. Thus, nebulisation by the nebuliser device can take place when the fluid is supplied to the nebuliser device under a negative pressure, which, as already stated above, leads to particularly good nebulisation results from the nebuliser device.

The present invention will now be described by means of advantageous embodiments and with reference to the following figures. The invention is not, however, restricted to the specific embodiments shown in the figures.

FIG. 1 shows an inhalation therapy device according to an embodiment of the present invention.

FIG. 2 shows an opening process of an ampoule by an opening means at various stages.

FIG. 3 shows various embodiments of ampoules with regard to design of ampoule body and opening area.

FIG. 4 shows an embodiment of the inhalation therapy device for opening the ampoule with the opening means.

FIG. 5 shows various embodiments of the seal of an ampoule against the opening means.

FIG. 6 shows squeezing of an ampoule according to an embodiment of the present invention.

FIG. 7 shows the negative pressure build-up inside an ampoule according to an embodiment of the present invention.

FIG. 8 shows the negative pressure build-up inside an ampoule according to another embodiment of the present invention.

FIG. 9 shows various embodiments of an ampoule for generation of a negative pressure in the ampoule.

FIG. 1 shows an advantageous embodiment of an inhalation therapy device 1 according to the present invention. The inhalation therapy device 1 comprises a nebuliser device 2, which nebulises a medicament advantageously provided in the form of a fluid 8 into a nebuliser chamber 12 such that an aerosol or mist 21 is provided in the nebuliser chamber 12. The patient or user can inhale the aerosol 21 generated by the nebuliser device 2 from the nebuliser chamber 12 via a mouthpiece 13. Valves in the form of inhalation or exhalation valves possibly required in the inhalation therapy device have not been included in FIG. 1 for reasons of clarity.

In the embodiment shown herein, the fluid 8 is provided in an ampoule 100 which, according to the invention, is closed before insertion into the inhalation therapy device. The ampoule 100 is inserted into an ampoule holder 3 which retains the fluid-containing ampoule 100. The inhalation therapy device 1 furthermore comprises an opening means 4 which serves to open the fluid-containing ampoule 100. The ampoule holder 3 advantageously comprises a first part 31 arranged so as to be displaceable in relation to the opening means 4 such that an ampoule 100 disposed in the ampoule holder can be moved in the direction of the opening means. The opening means is configured such that it opens the ampoule 100 when the one part 31 of the ampoule holder 3 is displaced. FIG. 1 shows that the one part 31 of the ampoule holder 3 moves inside the inhalation therapy device 1, however it is also conceivable for the opening means 4 to move inside the inhalation therapy device and for the one part 31 of the ampoule holder 3 to be stationary. As shown in FIG. 1, the inhalation therapy device 1 includes a body 10 having nebuliser device 2, nebuliser chamber 12 into which fluid 8 is to be nebulised by the nebuliser device 2, and opening means 4.

The ampoule holder 3 with its one moveable part 31 is advantageously disposed in a lid 5 of the inhalation therapy device in order to retain therein the ampoule 100 with the fluid 8 disposed therein. According to the invention, the patient or user inserts the ampoule 100 into the ampoule holder 3 in the still sealed state when the lid 5 is removed from the inhalation therapy device 1. The one part 31 of the ampoule holder 3 is then in a first position in which it advantageously holds the ampoule 100 such that it is still positioned at a distance from the opening means 4 when the lid 5 is placed on the inhalation therapy device. The one part 31 of the ampoule holder 3 is designed such that it moves the ampoule 100 in the direction of the opening means 4 when the lid 5 is closed by means of a pushing, turning or screwing movement, thereby causing the ampoule 100 to be opened by the opening means 4.

The opening means 4 advantageously comprises a cutter 42 for this purpose, which cuts into a wall area 130 of the ampoule 100 when the ampoule 100 is moved by the part 31 of the ampoule holder 3. The lid 5 of the inhalation therapy device is advantageously guided during these movements by a suitable device such that the ampoule 100 is advantageously no longer able to tilt in relation to the opening means 4. Once the ampoule 100 has been moved in the direction of the opening means 4 by the one part 31 of the ampoule holder 3, the cutter 42 cuts into a wall area 130 of the ampoule 100 when further displacement takes place such that the ampoule is opened at this moment. The cutter 42 of the opening means 4 is advantageously designed and arranged such that it does not completely separate the wall area 130 of the ampoule 100, but at least part of the wall area 130 of the ampoule 100 remains as a connection to the ampoule 100 so that this wall area 130 does not unintentionally reach the area of the inhalation therapy device 1.

The cutter 42 is advantageously disposed on an edge of the opening means 4 in such a manner that in one plane, the cutter 42 is disposed perpendicular to the axial direction or angled thereto. The cutter 42 can be smooth, corrugated or serrated in order to better open or cut into the wall area 130 of the ampoule.

The opening means 4 is advantageously configured as a needle which can pierce the provided areas of an appropriately designed ampoule 100 such that a fluid 8 disposed in the ampoule 100 can reach the nebuliser device.

The inhalation therapy device is advantageously provided with a supply means 6, via which a fluid 8 disposed in the ampoule 100 can reach the nebuliser device 2 from said ampoule 100 so that it can be nebulised thereby.

Although FIG. 1 shows a nebuliser device of the membrane nebuliser type, a nebuliser of the compressed air/nozzle nebuliser type or the ultrasound nebuliser type or other known types of nebuliser can also be used, which can also make use of the subject matter of the present invention.

The opening means 4 advantageously comprises a conduit 41 that extends at least partly in a longitudinal direction and via which the fluid 8 from the ampoule 100 can reach the nebuliser device 2 or the supply means 6. It can be achieved in this manner that the fluid can reach the nebuliser device 2 via the conduit 41 extending in the interior of the opening means 4 without loss due to leakage. However, it is alternatively also conceivable to design the opening means 4 such that it does not have an explicit conduit 41 extending in its interior, but rather such that the fluid can reach the nebuliser device 2 along other areas exposed by the opening means 4, for example grooves or slots which can be provided on the outside of the opening means 4.

FIG. 2 shows details of the opening process of the ampoule 100 according to an advantageous embodiment of the present invention.

FIG. 2*a* thereby shows the wall area 130 of the fluid-containing ampoule 100, which is intended for opening, before this area comes together with the opening means 4. In this embodiment, the opening means 4 comprises a cutter 42 which is formed at the end of a conduit 41 via which the fluid 8 disposed in the ampoule 100 reaches the nebuliser device as shown in FIG. 1. The wall area 130 of the ampoule 100 that is intended for opening advantageously has at least one predetermined breaking point 131, at which the ampoule 100 is specifically opened.

FIG. 2*b* shows a position of the fluid-containing ampoule 100 just after it has come into contact with the opening means 4. The cutter 42 of the opening means 4 has thereby already slightly cut into or broken open the wall area 130 of the ampoule 100 at the predetermined breaking point 131, however not yet so far that a fluid 8 disposed in the ampoule 100 can arrive in the opening channel or conduit 41 of the opening means 4. Both the wall area 130 of the ampoule 100 and the ampoule 100 itself, however also the opening means 4, are advantageously designed such that the opening means 4 tightly seals for the time being the already opened area of the ampoule 100 so that no fluid 8 can accidentally escape. The wall area 130 advantageously does not expose the channel or conduit 41 until the ampoule 100 is almost completely opened and sealed.

FIG. 2*c* shows a more advanced opening of the ampoule 100, in which the wall area 130 has already been cut to a greater extent, however is still in such a position that it closes off the conduit 41 of the opening means 4 so that no fluid 8 from the ampoule 100 can escape into the conduit 41 of the opening means 4. The ampoule advantageously forms a seal in against the opening means 4 at a sealing surface 143 provided for this purpose.

FIG. 2*d* shows the ampoule 100 disposed on the opening means 4 in an already completely opened state so that the fluid 8 disposed in the ampoule 100 can reach the inhalation therapy device via the conduit 41. The wall section 130 of the ampoule 100 is thereby completely opened, however advantageously not separated from the ampoule 100. The surface 143 of the ampoule provided for sealing thereby forms a seal at the opening means 4 such that the fluid can only escape from the ampoule 100 via the conduit 41, however not between the opening means 4 and the ampoule 100. A ventilation channel may be provided for easier flow of the fluid out of the ampoule 100, which, for example, guides displaced air out of the conduit 41 and into the ampoule, thus aiding the exit of the fluid from the ampoule 100.

FIG. 3 shows various embodiments of an ampoule which differ with regard to the opening area 130 and the area which is accommodated in the ampoule holder 3 and at which the ampoule 100 is retained in the ampoule holder 3. Positioning and retention are important so that the ampoule 100 can be opened precisely in a defined movement process such that it forms a seal with the opening means 4.

FIG. 3*a* shows an ampoule 100 filled with a fluid 8 and having a first area 110 that is designed so as to open upon displacement in the direction of the opening means 4, advantageously in a wall area 130 of the ampoule, such that a fluid 8 disposed in the ampoule 100 reaches the inhalation therapy device. The ampoule 100 furthermore comprises a second area 120 which is configured such that following insertion, a part 32 of the ampoule holder 3 grips this and retains the ampoule. In the embodiment shown in FIG. 3*a*, the ampoule 100 is designed such that it is retained securely by the ampoule holder 3 by means of clamping. The ampoule 100 can be filled completely with a fluid 8 such that there is no further gas space in the ampoule 100.

FIG. 3*b* shows an ampoule 100 that is only partly filled with a fluid 8 and additionally still has a gas space 180. This allows the amount of medicament to be dosed precisely without deviating from a standard ampoule size.

The ampoule 100 shown in FIG. 3*b* comprises an indentation or recess 121 in the holding area 120 of the ampoule 100, which enables the ampoule to be retained securely by engaging in an ampoule holder 3 equipped with suitably designed projections, without the ampoule 100 unintentionally slipping out of the ampoule holder 3. The indentation or recess can be a circumferential channel or a recess that is restricted to peripheral segments. The wall area 130 of the ampoule 100 comprising predetermined breaking points 131 at which the ampoule is specifically opened, is disposed in an area 110 of the ampoule. Advantageously disposed close to this opening wall area 130 is a sealing surface 143 which is designed such that the ampoule 100 forms a seal at the opening means 4 such that no fluid 8 can escape from the ampoule 100.

FIG. 3*c* shows an ampoule similar to the one shown in FIG. 3*b*, however instead of an indentation 121, the ampoule 100 shown in FIG. 3*c* has a circumferential bead 122 or a bead provided only in certain areas. This bead 122 has essentially the same purpose as the recess 121, however the bead can also easily prevent the ampoule from being inserted further into the ampoule holder 3 than intended.

FIG. 3*d* shows an ampoule having an area 111 which can be squeezed such that when the ampoule 100 is squeezed, a positive pressure is generated in the ampoule 100. Since the fluid 8 filled in the ampoule is generally incompressible, the pressure in the gas space 180 of the ampoule increases upon squeezing.

FIG. 4 shows embodiments of an inhalation therapy device in which the ampoule 100 in an ampoule holder 3 is moved on a substantially straight path in the direction of the opening means 4. For this purpose, the first part 31 of the ampoule holder 3 is, for example, provided, as shown in FIG. 4, with helically running grooves 35 in which engage pins 34 that are located in a second part 32 of the ampoule holder. Only one of these pins 34 is visible in FIG. 4. When the second part 32 of the ampoule holder is twisted in relation to the first part 31, the pins 34 in collaboration with grooves 35 cause the first part to move as depicted in FIG. 4 with the double arrow. To support this movement and to prevent the first part 31 from also twisting, rods 33 are provided in the shown embodiment, which are arranged so as to be moveable in channels 33a of the first part 31. In this way, the first part 31 of the ampoule holder 3 moves in a straight line and shifts the ampoule 100 held in this first part in the direction of the opening means 4. It must be noted that in this case of a straight movement, the opening means 4 advantageously comprises a cutter 42 that is angled in relation to the direction of movement, so that the opening process as shown in connection with FIG. 2 occurs.

Figure 4B:
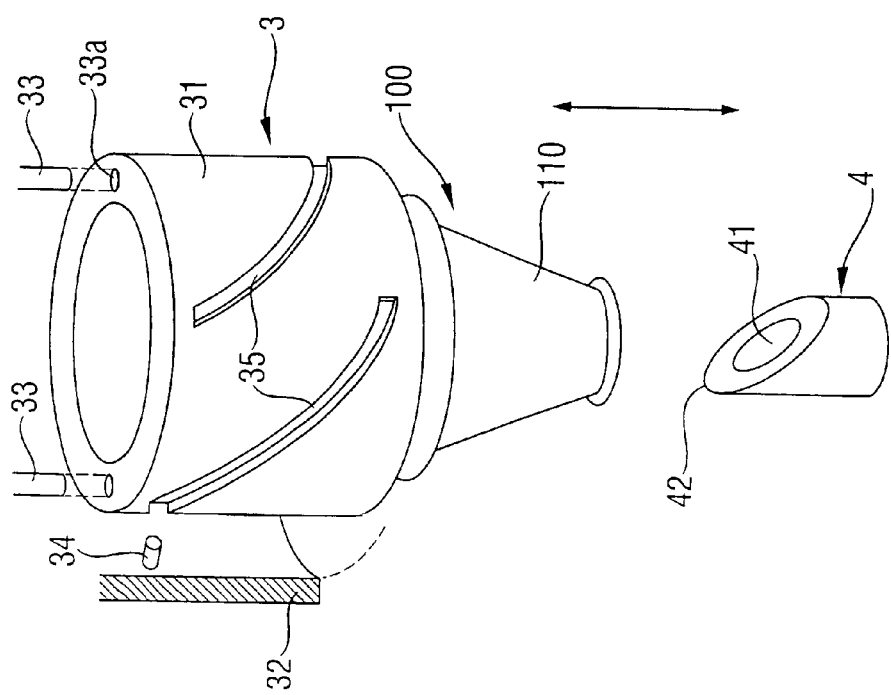

According to a further embodiment shown in FIG. 4b, the opening means 4 comprises a cutter 42 which is arranged perpendicular to the direction of movement and which surrounds an orifice 41 in a plane running substantially perpendicular to the longitudinal axis of the opening means 4. In order to form the cutter 42, the upper area of the wall of the opening means 4 advantageously slopes inward, as shown in FIG. 4b, or outward in a cone shape. In this case, the ampoule 100 in the ampoule holder 3 is also moved in a straight line towards the opening means 4, however a circular movement is superposed so that the opening means 4 can cut into and seal the correspondingly provided area of the ampoule. The simultaneous linear and rotational movement can be achieved by a corresponding design of the parts of the ampoule holder. Furthermore, the cutter 42 is advantageously corrugated or serrated in this embodiment according to FIG. 4.

FIG. 5 shows various forms of the sealing of the ampoule 100 against the opening means 4.

FIG. 5a shows an embodiment in which the ampoule 100 directly abuts an outer surface, preferably the side surface, of the opening means 4. By means of an appropriate design of the ampoule 100 and the opening means 4, sealing of the ampoule at the opening means 4 can thus be achieved without additional sealing elements or sealing materials having to be provided. An advantageous material combination is thereby an opening means made of a hard material and an ampoule made of a softer material so that the softer material of the ampoule can adapt to the hard material of the opening means 4 in order to ensure a sufficient seal of the ampoule against the inhalation therapy device.

FIG. 5b shows an embodiment having a cone-shaped extension of the opening means 4 so that when the opening means 4 is inserted in the ampoule 100, the forces on the inner ampoule-side sealing surface 143 of the ampoule 100 increase and the seal is thus improved. The conical part of the opening means 4, as the device-side sealing surface 43 of the opening means 4, is pressed against the ampoule-side sealing surface 143 of the ampoule 100 and an improved seal of the ampoule opening against the opening means 4 is achieved.

FIG. 5c shows an embodiment in which a separate sealing element 44, which can be provided, for example, on the inhalation therapy device, seals the opening means 4 against an ampoule 100. Both the ampoule-side sealing surface 143 of the ampoule 100 and the device-side sealing surface 43 of the inhalation therapy device thereby engage on the sealing element 44.

FIG. 5d shows a sealing element 44, for example an O-ring, which is embedded in a recess in order to securely position the sealing element. The device-side sealing surface 43 of the inhalation therapy device is located in this recess. Both the device-side sealing surface 43 of the inhalation therapy device, more specifically of the opening means, and the ampoule-side sealing surface 143 of the ampoule end at the sealing element 44 so as to form a seal. In addition to the embodiments shown in FIGS. 5c and 5d, the sealing element 44 can also be glued to the inhalation therapy device so that the sealing element cannot be lost. The sealing element 44 can alternatively also be provided on the ampoule so as to give configurations which are geometrically similar to those in FIGS. 5c and 5d. Owing to the use of a separate sealing element 44, sealing can also be achieved even if fit-sealing as in FIG. 5a or compression-sealing as in FIG. 5b is not possible, for example in the case of a glass ampoule.

Figure 6C:
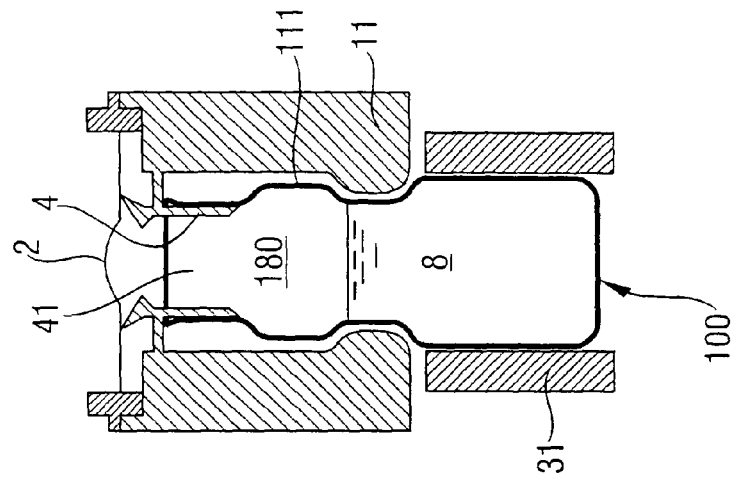
Figure 6B:
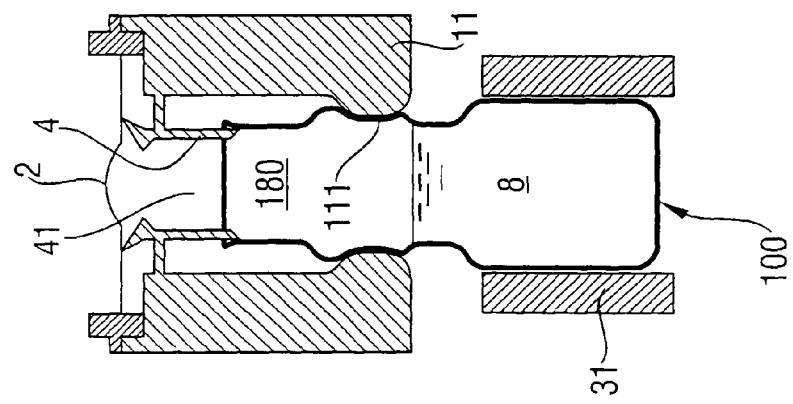
Figure 6A:
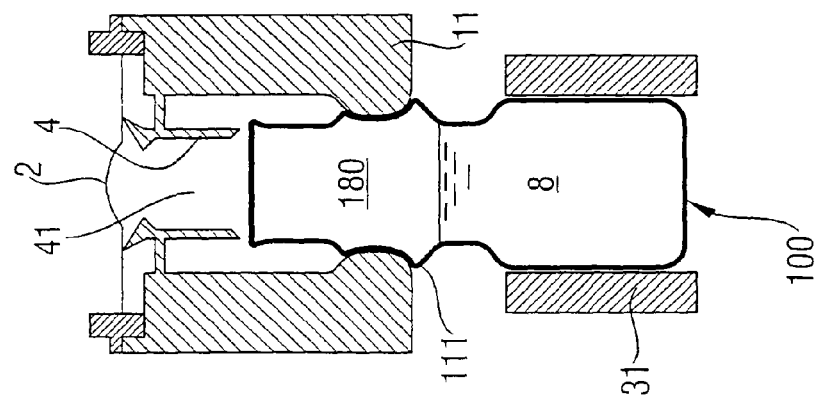

FIG. 6 shows an embodiment of the present invention in which the ampoule is provided with a squeezing means 11. The squeezing means 11 squeezes an ampoule correspondingly provided with a squeezing area 111 such that a positive pressure develops in the ampoule. The ampoule 100 advantageously has a gas space 180 for this purpose. The squeezing of the ampoule 100 by the squeezing device 11 generates a positive pressure in the gas space 180, which can then escape via the opening means 4 when the ampoule is opened. When the ampoule 100 is subsequently sealed against the opening means 4, the interior of the ampoule is sealed in relation to the opening means such that when squeezing is stopped, a negative pressure develops in the gas space 180 which is under normal pressure after venting. In this way it can be achieved that a negative pressure prevails in the ampoule 100. As stated above, the formation of droplets on the membrane of a membrane nebuliser can be prevented in this manner. A negative pressure that is advantageous for nebulisation is thus generated in the ampoule with the squeezing means 11, which, upon insertion of the ampoule, first squeezes the ampoule and which, after elimination of the resulting positive pressure in the ampoule and sealing of the ampoule, stops squeezing again.

FIG. 7 shows a further embodiment of an inhalation therapy device with an ampoule holder 3 and a correspondingly designed ampoule 100 which allows generation of a negative pressure in the gas space 180 of the ampoule 100. According to this embodiment, the risk of fluid loss is reduced. The first area 110 of the ampoule 100 and the second area 120 of the ampoule are arranged so as to be moveable in relation to one another such that in a hermetically sealed ampoule 100, a negative pressure can be generated in the gas space 180 of the ampoule upon movement of the first area 110 of the ampoule 100 in relation to the second area 120 of the ampoule 100. The first area of the ampoule 100 and second area of the ampoule 120 are advantageously connected with one another by a resilient element 150.

According to the embodiment shown in FIG. 7, the second part 32 of the ampoule holder 3 holds the ampoule at the second area 120 of the ampoule 100. As FIGS. 7*a* and 7*b* show, the first part 31 of the ampoule holder 3 is formed so as to be movable in relation to the second part 32 of the ampoule holder 3. The first part 31 of the ampoule holder 3 is designed so that it acts on the first area 110 of the ampoule 100 so that a movement of the first part 31 leads to a movement of the first area 110 of the ampoule in relation to the second area 120 of the ampoule. The two areas of the ampoule 100 are thereby moved in relation to each other, which is possible owing to the resilient element 150. Upon movement of the first area 110 of the ampoule 100, the opening means 4 opens the ampoule 100 as shown in FIG. 7b.

For engagement of the first part 31 of the ampoule holder 3, the first area 110 of the ampoule 100 is advantageously formed as a collar 160 as shown in FIG. 7. The collar 160 advantageously has a diameter which is greater, at least at one point, than the diameter of the ampoule body, as indicated by dashed lines in FIG. 7. In this way, the ampoule 100 can be inserted in the ampoule holder 3 shown in FIG. 7 so that the first part 31 of the ampoule holder 3 can engage on this collar 160 in order to move the first area 110 of the ampoule 100 in relation to the second area 120 of the ampoule 100. The function of the collar can be assumed by corresponding webs or other projections.

FIG. 7a shows the ampoule 100 inserted in the ampoule holder 3, the first part 31 of the ampoule holder 3 being in a position in which it does not yet engage on the first area 110 of the ampoule 100. In this state, the ampoule, in particular the first area 110 of the ampoule 100, is still at a distance from the opening means 4. When the first part 31 of the ampoule holder 3 is moved, the first part 31 engages on the first area 110 of the ampoule 100 and moves this in relation to the second area 120 of the ampoule 100. Since the second part 32 of the ampoule holder 3 retains the second area 120 of the ampoule 100, the movement causes an enlargement of ampoule volume so that a negative pressure develops in the ampoule 100. The resilient part 150 connecting the first area 110 with the second area 120 is thus stretched.

In the embodiment shown in FIG. 7, the first part 31 of the ampoule holder 3 is displaceable, according to the invention, in relation to the opening means 4.

FIG. 8 shows a further embodiment of an inhalation therapy device comprising an ampoule holder 3 and a correspondingly designed ampoule 100 which allows the generation of a negative pressure in the gas space 180 of the ampoule 100 and reduces the risk of fluid loss.

FIG. 8a shows the ampoule 100 inserted in the ampoule holder 3. In this state, the ampoule, in particular the first area 110 of the ampoule 100, is still at a distance from the opening means 4. According to the invention, the first part 31 of the ampoule holder 3 is arranged also in this embodiment so as to be displaceable in relation to the opening means 4 such that upon displacement of the first part 31 of the ampoule holder 3, the opening means 4 opens the ampoule 100 in the ampoule holder 3. On transition from the position shown in FIG. 8a to the position shown in FIG. 8b, the first part 31 of the ampoule holder 3 according to this embodiment is moved together with the ampoule holder 3 with which it is firmly connected. During this movement, the opening means 4 opens the ampoule 100.

According to the embodiment shown in FIGS. 8a, 8b and 8c, the second part 32 of the ampoule holder 3 retains the ampoule 100 at the second area 120 of the ampoule 100. The second part 32 of the ampoule holder 3 is formed so as to be displaceable in relation to the first part 31 of the ampoule holder 3. The second part 32 of the ampoule holder 3 is designed so that it engages on the second area 120 of the ampoule 100 such that a movement of the second part 32 leads to a movement of the second area 120 of the ampoule in relation to the first area 110 of the ampoule. As a result, the two areas of the ampoule 100 are moved in relation to each other, which is possible owing to the resilient element 150. If the second part 32 of the ampoule holder 3 is moved, the first part 31 engages on the first area 110 of the ampoule 100 and on movement of the second area 120 in relation to the first area 110 of the ampoule 100, holds this in the position on the opening means 4. FIG. 8c shows the position of the second part 32 of the ampoule holder 3 with the engaged second area 120 of the ampoule 100 after movement of the second part 32 and the first part 31 of the ampoule holder 3 in relation to one another. Since the first part 31 of the ampoule holder 3 retains the first area 110 of the ampoule 100, the movement causes an enlargement of the ampoule volume so that a negative pressure develops in the ampoule 100. The resilient part 150 connecting the first area 110 with the second area 120 is hereby extended.

FIG. 9 shows two embodiments of an ampoule 100 with a resilient area 150, each in the state at rest and in the extended or stretched state.

Figure 9D:
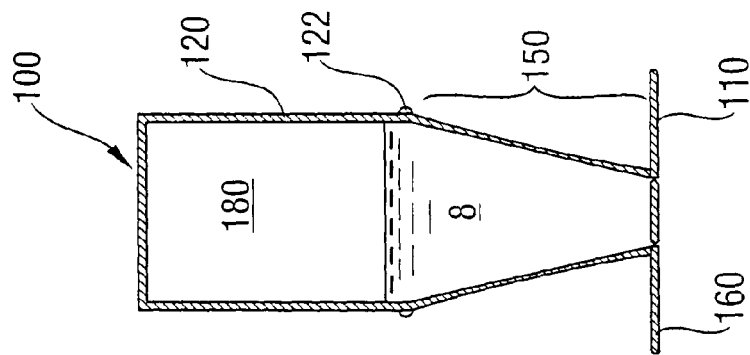
Figure 9C:
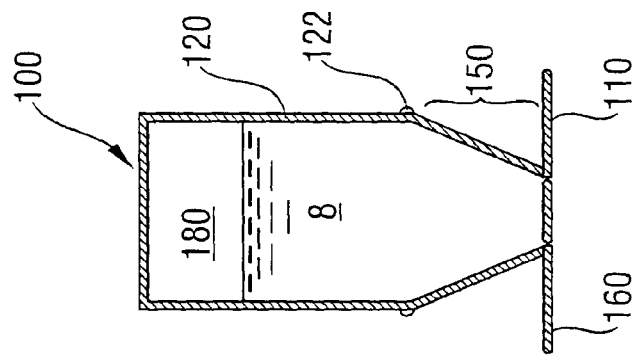
Figure 9B:
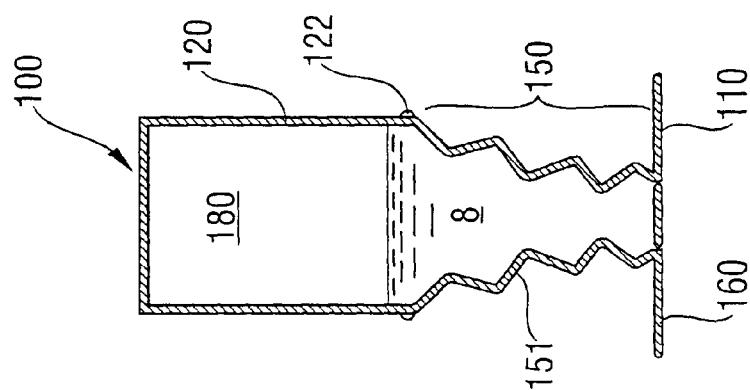
Figure 9A:
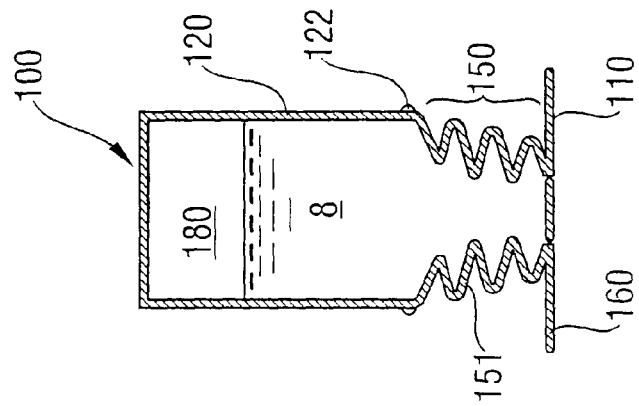

FIG. 9a shows an ampoule 100, the first area 110 of which is connected with a second area 120 by bellows 151. FIG. 9b shows the ampoule of FIG. 9a in a state in which the first area 110 of the ampoule 100 has been moved in relation to the second area 120 of the ampoule 100. As can be seen from a comparison of FIGS. 9a and 9b, the bellows 151 are extended.

FIG. 9c shows an ampoule 100 in which the resilient area 150 connecting the first area 110 of the ampoule 100 with the second area 120 of the ampoule 100, consists of a stretchable material. This area 150 changes in length on movement of the first area 110 in relation to the second area 120, as shown in FIG. 9d.

FIGS. 7 and 9 show an integral design of the ampoule 100 in one material. However, areas 110, 120 and 150 of the ampoule can also be made of different materials, in particular plastics. The areas, which have different degrees of rigidity and resilience, can nevertheless be formed as a single unit for example by joining them together by way of the moulding of rigid and resilient materials together.

The invention claimed is:

1. Inhalation therapy device comprising:
   a body having a nebuliser device, a nebuliser chamber into which a fluid is to be nebulised by the nebuliser device, and an opening means;
   a lid,
   an ampoule holder for retaining an ampoule containing the fluid to be nebulised and to be opened by the opening means, the ampoule holder comprising at least one part configured to be displaced relative to the lid in response to the lid closing on the body
   wherein the ampoule holder is arranged in the lid so that the ampoule is moved in a direction of the opening means and is opened by the opening means in response to closing of the lid on the body, such that the opening means opens the ampoule disposed in the ampoule holder so that substantially all the fluid contained in the ampoule reaches the nebuliser device, wherein the ampoule holder has a first end and a second end, wherein the opening means and the nebuliser device are located at the first end of the ampoule holder and wherein the opening means has a conduit through which the fluid from the ampoule reaches the nebuliser device.

2. Inhalation therapy device according to claim 1, wherein the opening means and the ampoule holder are displaceable in relation to one another along a substantially straight, circular or helical path.

3. Inhalation therapy device according to claim 1, wherein the opening means has a cutter designed to cut, when displacement of the ampoule occurs, into a wall area of the ampoule that is intended for opening.

4. Inhalation therapy device according to claim 1, wherein the opening means is integrally connected with the conduit.

5. Inhalation therapy device according to claim 1, wherein the inhalation therapy device has a sealing device for sealing the ampoule against the opening means.

6. Inhalation therapy device according to claim 1, wherein the opening means is configured to seal an opening of the ampoule to the opening means.

7. Inhalation therapy device according to claim 1, wherein the inhalation therapy device comprises a squeezing means which is designed to create a positive pressure in the ampoule to squeezedly hold the ampoule in a displaced position.

8. Inhalation therapy device according to claim 7, wherein the ampoule holder comprises the squeezing means and the squeezing means is formed such that it squeezes the ampoule during opening.

9. Inhalation therapy device according to claim 1, wherein the ampoule holder has a first part designed such that it engages with the ampoule only when displacement of the first part relative to the lid occurs and a second part designed to hold the ampoule.

10. Inhalation therapy device according to claim 9, wherein the first part of the ampoule holder and the second part of the ampoule holder are formed so as to be moveable in relation to one another so that the first part of the ampoule holder acting on a first part of the ampoule and the second part of the ampoule holder acting on a second part of the ampoule move, when displacement of the first part relative to the lid occurs, the first part and the second part of the ampoule in relation to one another such that a negative pressure or a positive pressure develops in the ampoule.

11. Inhalation therapy device according to claim 1, further comprising the ampoule, wherein the ampoule has a first area designed for opening by the opening means and a second area designed for holding by the ampoule holder.

12. Inhalation therapy device according to claim 11, wherein the ampoule comprises a sealing surface designed to seal the ampoule against the opening means or the conduit.

13. Inhalation therapy device according to claim 11, wherein the first area of the ampoule is arranged so as to be moveable in relation to the second area of the ampoule.

14. Inhalation therapy device according to claim 11, wherein the first area of the ampoule is connected with the second area of the ampoule by a resilient element or bellows.

15. Inhalation therapy device according to claim 1, wherein the nebuliser device comprises a membrane nebuliser.

16. Inhalation therapy device comprising:
a body having a nebuliser device, a nebuliser chamber into which a fluid is to be nebulised by the nebuliser device, and a needle,
a lid,
an ampoule holder for retaining an ampoule containing the fluid to be nebulised and to be opened by the needle, the ampoule holder comprising at least one part configured to be displaced relative to the lid in response to the lid closing on the body
wherein the ampoule holder is arranged in the lid so that the ampoule is moved in a direction of the needle and is opened by the needle in response to closing of the lid on the body, such that the needle opens the ampoule disposed in the ampoule holder so that substantially all the fluid contained in the ampoule reaches the nebuliser device, wherein the ampoule holder has a first end and a second end, wherein the needle and the nebuliser device are located at the first end of the ampoule holder and wherein the needle has a conduit through which the fluid from the ampoule reaches the nebuliser device.

17. Inhalation therapy device comprising:
a body having a nebuliser device, a nebuliser chamber into which a fluid is to be nebulised by the nebuliser device, and an opening means,
a lid,
an ampoule holder for holding an ampoule containing the fluid to be nebulised and to be opened by the opening means,
wherein the ampoule holder is arranged in the lid and wherein the ampoule holder moves relative to the lid to move the ampoule in a direction of the opening means and the opening means opens the ampoule in response to closing of the lid on the body, such that the opening means opens the ampoule disposed in the ampoule holder so that substantially all the fluid contained in the ampoule reaches the nebuliser device, wherein the ampoule holder has a first end and a second end, wherein the opening means and the nebuliser device are located at the first end of the ampoule holder and wherein the opening means has a conduit through which the fluid from the ampoule reaches the nebuliser device.

\* \* \* \* \*